US012023129B2

United States Patent
Ishikawa et al.

(10) Patent No.: US 12,023,129 B2
(45) Date of Patent: Jul. 2, 2024

(54) OPTICAL MEASUREMENT SYSTEM AND OPTICAL BRAIN FUNCTION MEASUREMENT METHOD

(71) Applicant: Shimadzu Corporation, Kyoto (JP)

(72) Inventors: Akihiro Ishikawa, Kyoto (JP); Yoshihiro Inoue, Kyoto (JP); Shumpei Yamaguchi, Kyoto (JP); Haruo Uno, Kyoto (JP); Takashi Amita, Kyoto (JP); Yoshinori Masuda, Otsu (JP); Haruhide Udagawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 504 days.

(21) Appl. No.: 15/313,958

(22) PCT Filed: May 20, 2014

(86) PCT No.: PCT/JP2014/063374
§ 371 (c)(1),
(2) Date: Nov. 24, 2016

(87) PCT Pub. No.: WO2015/177876
PCT Pub. Date: Nov. 26, 2015

(65) Prior Publication Data
US 2017/0143212 A1    May 25, 2017

(51) Int. Cl.
*A61B 5/00* (2006.01)
*A61B 5/1455* (2006.01)

(52) U.S. Cl.
CPC .......... *A61B 5/0082* (2013.01); *A61B 5/0075* (2013.01); *A61B 5/14553* (2013.01);
(Continued)

(58) Field of Classification Search
None
See application file for complete search history.

(56) References Cited

U.S. PATENT DOCUMENTS

| 6,542,763 | B1 * | 4/2003 | Yamashita | ........... A61B 5/0059 600/310 |
| 7,171,250 | B2 | 1/2007 | Yamamoto et al. | |

(Continued)

FOREIGN PATENT DOCUMENTS

| CN | 1660017 A | 8/2005 |
| CN | 101943904 A | 1/2011 |

(Continued)

OTHER PUBLICATIONS

Wireless LAN by Wikipedia; pub. online on May 8, 2014 at <https://en.wikipedia.org/w/index.php?title=Wireless_LAN&oldid=607603740> (Year: 2014).*

(Continued)

*Primary Examiner* — Pascal M Bui Pho
*Assistant Examiner* — Michael S Kellogg
(74) *Attorney, Agent, or Firm* — Muir Patent Law, PLLC

(57) ABSTRACT

This optical measurement system 100 is provided with a plurality of optical measurement units 1 and a control device 2 that controls the optical measurement unit. The control device includes a communication unit 24 that obtains specific state information 30 on whether or not the optical measurement unit is in a measurable state by communication for each of a plurality of optical measurement units, a display unit 25 that collectively displays the obtained state information for each of the plurality of optical measurement units, and a control unit 21 that controls a plurality of optical measurement units so that a simultaneous measurement is performed.

8 Claims, 8 Drawing Sheets

(52) U.S. Cl.
CPC .......... *A61B 5/4064* (2013.01); *A61B 5/6803* (2013.01); *A61B 5/742* (2013.01); *A61B 5/7435* (2013.01)

(56) References Cited

U.S. PATENT DOCUMENTS

| | | | |
|---|---|---|---|
| 7,805,263 B2 | 9/2010 | Mack | |
| 8,755,867 B2 | 6/2014 | Inoue et al. | |
| 2007/0255155 A1* | 11/2007 | Drew | A61B 5/0031 600/523 |
| 2008/0114239 A1* | 5/2008 | Randall | A61B 8/4438 600/437 |
| 2008/0259301 A1 | 10/2008 | Yasuda et al. | |
| 2009/0318785 A1* | 12/2009 | Ishikawa | A61B 5/0476 600/310 |
| 2010/0085891 A1 | 4/2010 | Kind et al. | |
| 2011/0250920 A1 | 10/2011 | Shimizu et al. | |
| 2012/0238883 A1* | 9/2012 | Inoue | A61B 5/0059 600/476 |
| 2013/0238792 A1 | 9/2013 | Kind et al. | |
| 2013/0262730 A1* | 10/2013 | Al-Ali | G16H 10/60 710/303 |
| 2014/0022256 A1* | 1/2014 | Carnes | A61B 5/14553 345/440.1 |

FOREIGN PATENT DOCUMENTS

| | | |
|---|---|---|
| CN | 102695459 A | 9/2012 |
| JP | 2004-316283 A | 11/2004 |
| JP | 2008-518711 A | 6/2008 |
| JP | 2011-024925 A | 2/2011 |
| WO | WO 2011/067833 | 6/2011 |

OTHER PUBLICATIONS

IEEE 802.11 by Wikipedia; pub. online on May 11, 2014 at <https://en.wikipedia.org/w/index.php?title=IEEE_802.11&oldid=608047899> (Year: 2014).*
Received signal strength indication by Wikipedia; pub. online on Sep. 9, 2013 at <https://en.wikipedia.org/w/index.php?title=Received_signal_strength_indication&oldid=572165758> (Year: 2013).*
Bluetooth by Wikipedia; pub. online on May 19, 2014 at <https://en.wikipedia.org/w/index.php?title=Bluetooth&oldid=609223854> (Year: 2014).*
P. H. Enslow, "What is a "Distributed" Data Processing System?," in Computer, vol. 11, No. 1, pp. 13-21, Jan. 1978, doi: 10.1109/C-M.1978.217901. (Year: 1978).*
Written Opinion by the International Search Authority issued Jul. 15, 2014 in PCT/JP2014/063374.
International Search Report issued Jul. 15, 2014 in PCT/JP2014/063374.
Communication mailed Dec. 5, 2018, from the Chinese Patent Office in corresponding Chinese Patent Application No. 201480078567.9 (9 pages).
English-language machine translation of Communication mailed Dec. 5, 2018, from the Chinese Patent Office in corresponding Chinese Patent Application No. 201480078567.9 (5 pages).
Third Office Action, dated Jun. 2, 2020, issued from the Chinese Patent Office in Chinese Patent Application No. 201480078567.9 (10 pages) and English-language machine translation of the same (12 pages).
Office Action, dated Sep. 2, 2019, issued from the Chinese Patent Office in Chinese Patent Application No. 201480078567.9 (10 pages) and English-language machine translation of the same (12 pages).

* cited by examiner

OPTICAL MEASUREMENT SYSTEM AND OPTICAL BRAIN FUNCTION MEASUREMENT METHOD

TECHNICAL FIELD

The present invention relates to an optical measurement system, and particularly to an optical measurement system equipped with an optical measurement unit for performing a brain function measurement and a control device for controlling the optical measurement unit, and an optical brain function measurement method.

BACKGROUND ART

Conventionally, an optical measurement system equipped with an optical measurement unit and a control device is known. Such optical measurement system is disclosed by, for example, WO 2011/067833.

The optical measurement system disclosed by the aforementioned WO 2011/067833 is equipped with a plurality of optical measurement units for performing a brain function measurement by a near-infrared spectroscopy (NIRS). The optical measurement unit is configured so as to be able to being carried by a subject in a state of being attached to the subject. The control of the measurement operation by the control device and the transmission of measurement data to the control device is performed by wireless communication.

Prior Art Document

PATENT DOCUMENT

Patent Document 1: WO 2011/067833

SUMMARY OF THE INVENTION

Problems to be Solved by the Invention

As applications of such optical measurement system, in the fields of a brain science research and a neuromarketing, there is a need that brain function measurements of a plurality of brains are carried out simultaneously in parallel using a plurality of optical measurement units (simultaneous measurement). For example, it can be considered to utilize the system such that respective brain activities of a group consisting of a plurality of subjects are measured in a comparable manner during communications.

In cases where a simultaneous measurement is performed using a plurality of (e.g., four or more) optical measurement units, it is initially required to make all of the optical measurement units to be used in measurable conditions. For example, it is necessary to establish communication connections between each of the optical measurement units and a control device or to charge or exchange batteries in the case of a battery driven optical measurement unit. Conventionally, however, it was necessary to independently confirm whether or not each optical measurement unit was in a measurable condition one by one. For this reason, conventionally, there were such problems that when performing a simultaneous measurement by a plurality of optical measurement units, the works for grasping the state of each of the plurality of optical measurement units were cumbersome, and it took a time for the measurement preparation.

The present invention was made to solve the aforementioned problems, and one of the objects of the present invention is to provide an optical measurement system and an optical brain function measurement method capable of shortening a time required for a measurement preparation by facilitating a grasp of a state of each optical measurement unit when performing a simultaneous measurement by a plurality of optical measurement units.

Means for Solving the Problems

To attain the aforementioned objects, an optical measurement system of a first aspect of the present invention includes:
- a plurality of optical measurement units that perform a brain function measurement; and
- one or a plurality of control devices that control the optical measurement unit,
- wherein the control device includes
- a communication unit that obtains specific state information on whether or not the optical measurement unit is in a state in which the optical measurement unit can perform a measurement for each of the plurality of optical measurement units,
- a display unit that collectively displays the state information obtained for each of the plurality of optical measurement units, and
- a control unit that controls the plurality of optical measurement units so that a simultaneous measurement is performed by a part or an entirety of the plurality of optical measurement units simultaneously in parallel.

In the optical measurement system of the first aspect of the present invention, as described above, by providing the communication unit that obtains the specific state information on whether or not the optical measurement unit is in a measurable state by communication for each of a plurality of optical measurement units and the display unit that collectively displays the obtained state information for each of the plurality of optical measurement units, a user can collectively confirm whether or not respective optical measurement units are in a measurable state at once from the state information displayed on the display unit of the control device. As a result, the user can quickly grasp the optical measurement unit which is not in a measurable state, and operations for making it in a measurable state can be performed. Further, it is also possible to collectively grasp measurable optical measurement units, and therefore as to the measurable optical measurement units, it is possible to quickly complete the preparation for the brain function measurement to a subject. From the above, according to the present invention, when performing a simultaneous measurement by a plurality of optical measurement units, it is possible to shorten the time required for the measurement preparation by facilitating the grasping of the state of each optical measurement unit.

In the optical measurement system according to the first aspect, preferably, the control unit of the control device is configured such that the optical measurement unit capable of performing a simultaneous measurement is specified based on the state information and information on whether or not the simultaneous measurement can be performed is displayed collectively on the display unit for each of the plurality of optical measurement units. By configuring as described above, for example, even in cases where the state information includes a plurality of items, a user can grasp whether or not each of the plurality of optical measurement units can perform a simultaneous measurement on the screen of the display unit at a glance. Further, it is not required for a user to consider the state information to judge whether or not each of the optical measurement units is in a measurable state, and it is possible to immediately distinguish between a unit which can perform a simultaneous measurement and a unit which cannot perform a simultaneous measurement by just looking at the display unit. As a result, it is possible to further facilitate grasping of the state of each optical measurement unit, and also possible to improve the convenience for a user.

In this case, preferably, the control device further includes an operation input section that accepts an individual selection operation for the optical measurement unit capable of performing the simultaneous measurement, and the control unit of the control device performs the simultaneous measurement by the optical measurement unit selected. By configuring as described above, in cases where, for example, only some of the plurality of optical measurement units are used, it is possible for a user to immediately start the brain function measurement only by selecting the optical measurement units which can perform a simultaneous measurement. With this, the measurement preparation time can be further shortened.

In the optical measurement system according to the aforementioned first aspect, preferably, the state information includes at least information on a communication state between the optical measurement unit and the control device, and information on a remaining battery capacity of the optical measurement unit. By configuring as described above, a user can collectively grasp, as state information, the information on the communication state required to make the optical measurement unit execute the measurement operation and the information of the remaining battery capacity on each optical measurement unit. With this, it becomes possible to easily and quickly grasp the information required to make each optical measurement unit in a measurable state.

In this case, preferably, the state information further includes at least one of the information on the remaining memory capacity of the optical measurement unit and the information on a received light quantity signal of the optical measurement unit. By structuring as described above, in cases where the information on the remaining memory capacity is included in the state information, it is possible to collectively grasp whether or not the remaining capacity for continuously measuring by each optical measurement unit is secured. When necessary, it is possible to take an action of, e.g., exchanging storage mediums. Further, in cases where the information on the received light quantity is included in the state information, it is possible to collectively grasp the information required to obtain excellent measurement data, such as, e.g., good or bad of the mounting state of the measuring terminals of each optical measurement unit to a subject, or a necessity of adjustment (calibration) of the light source and the light detection unit. When necessary, it is possible to take actions, such as, e.g., a re-mounting operation to a subject and an adjustment of the light source and the light detection unit. As a result, it becomes possible to grasp not only the information required to make each optical measurement unit in a measurable state but also the information required to obtain excellent measurement data by each optical measurement unit.

In the configuration in which the state information includes at least the information on communication state and the information on the remaining battery capacity, preferably, a control unit of the control device is configured to calculate each measurement possible time of the optical measurement unit based on at least the remaining batter capacity, calculate a simultaneous measurement possible time when a simultaneous measurement is performed by the plurality of optical measurement units based on respective measurement possible times of the plurality of optical measurement units, and display the simultaneous measurement possible time on the display unit. By configuring as described above, it is possible for a user to easily judge whether or not it is possible to perform a simultaneous measurement along the user's execution plan based on the simultaneous measurement possible time. When the simultaneous measurement possible time is insufficient, a user can take an action of changing a battery of the optical measurement unit in which the remaining battery capacity remains to some degrees or changing the execution plan of the measurements. With this, it is possible to further improve the convenience to the user.

In this case, preferably, the control unit of the control device obtains each of the state information of the optical measurement units during the measurement operation after initiation of the simultaneous measurement, calculate the measurement possible time, and displays information showing the optical measurement unit in which the measurement possible time has become smaller than a predetermined value. By configuring as described above, even in cases where the simultaneous measurement by a plurality of optical measurement units are being executed, when the measurement possible time of the optical measurement unit has become short, the user can grasp the optical measurement unit. With this, it is possible to take actions, such as, e.g., an action of connecting the unit in which the measurement possible time has become short to an external power source and an action of changing the execution plan of the measurement to interrupt the measurement at an appropriate timing. With this, it is possible to further improve the convenience to the user.

The optical brain function measurement method according to the second aspect of the present invention includes:

a step of obtaining specific state information on whether or not an optical measurement unit is in a measurable state for each of a plurality of optical measurement units;

a step of collectively displaying the state information obtained on a display unit for each of the plurality of optical measurement units; and a step of controlling a plurality of optical measurement units so that a simultaneous measurement is performed by a part or an entirety of the plurality of optical measurement units simultaneously in parallel.

In the optical brain function measurement method of the second aspect of the present invention, as described above, by providing the step of obtaining the specific state information on whether or not the optical measurement unit is in a measurable state by communication for each of a plurality of optical measurement units and a step of collectively displaying the obtained state information on the display unit for each of the plurality of optical measurement units, a user can collectively confirm whether or not respective optical measurement units are in a measurable state at once from the state information displayed on the display unit of the control device. As a result, the user can quickly grasp the optical measurement unit which is not in a measurable state, and operations for making it in a measurable state can be performed. Further, it is also possible to collectively grasp measurable optical measurement units, and therefore as to the measurable optical measurement units, it is possible to quickly complete the preparation for the brain function measurement to a subject. From the above, according to the present invention, when performing a simultaneous measurement by a plurality of optical measurement units, it is possible to shorten the time required for the measurement preparation by facilitating the grasping of the state of each optical measurement unit.

Effects of the Invention

As described above, according to the present invention, when performing a simultaneous measurement by a plurality of optical measurement units, it is possible to shorten the time required for the measurement preparation by facilitating the grasping of the state of each optical measurement unit.

EMBODIMENTS FOR CARRYING OUT THE INVENTION

Hereinafter, embodiments will be described base on drawings.

First Embodiment

Initially, with reference to FIGS. 1 to 5, an entire configuration of an optical measurement system 100 according to one embodiment of the present invention will be described.

Figure 1:
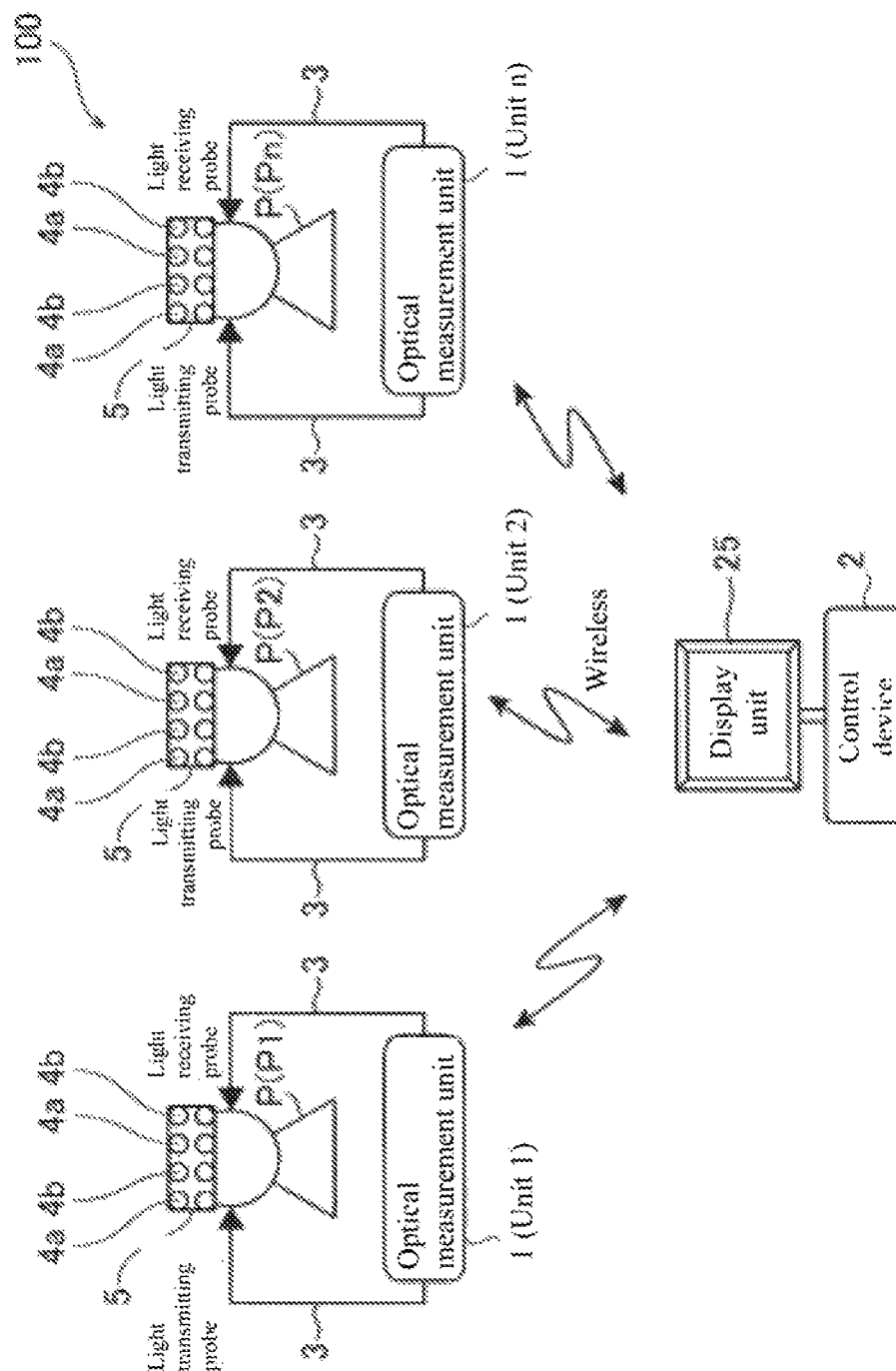
FIG. 1 is a schematic view showing an entire configuration of an optical measurement system according to a first embodiment of the present invention.

As shown in FIG. 1, the optical measurement system 100 of the first embodiment is configured as a system capable of performing a simultaneous measurement in which brain function measurements to a plurality of subjects P (P1 to Pn) are performed simultaneously in parallel by a plurality of optical measurement units 1. The optical measurement system 100 is configured by a plurality (n) of optical measurement units 1 (Unit 1 to Unit n) and a single control device 2 that controls the optical measurement units 1.

The optical measurement unit 1 is a device for measuring a brain activity of a subject P non-invasively, and is an optical measurement device that performs an optical measurement of a brain activity by a near-infrared spectroscopy (NIRS). In the first embodiment, the optical measurement unit 1 is configured as a portable unit capable of being carried by a subject P. Further, the plurality of optical measurement units 1 and the control device 2 are wirelessly connected so that intercommunications can be performed. With this, in the optical measurement system 100 according to the first embodiment, even during a brain function measurement, a subject will not be required to be in the vicinity of the control device 2, and therefore the subject P can freely move while carrying the optical measurement unit 1. This enables performing of a brain function measurement in an environment close to daily activities.

The plurality of optical measurement units 1 each have the same configuration. The optical measurement unit 1 is equipped with light transmitting probes 4a and light receiving probes 4b connected by optical fibers 3. To the optical measurement unit 1, a plurality of light transmitting probes 4a and a plurality of light receiving probes 4b can be connected, respectively. The light transmitting probe 4a and the light receiving probe 4b are detachably attached to a probe fixing holder 5 to be mounted on a head of a subject P.

The light transmitting probe 4a and the light receiving probe 4b have a function of detecting a signal showing a brain activity. The light transmitting probe 4a and the light receiving probe 4b are arranged on a head surface of a subject P by being attached to a holder 5. The optical measurement unit 1 irradiates measurement light in a wavelength region of near-infrared light from the light transmitting probe 4a and detects the measurement light reflected in a head of a subject P by making the reflected light incident to the light receiving probe 4b to obtain a strength (received light quantity) of the measurement light. Based on the strength of the obtained measurement light, the change of the amount of hemoglobin (oxygenated hemoglobin, deoxygenated hemoglobin, and total hemoglobin) accompanied by a brain activity can be obtained. With this, the optical measurement system 100 can non-invasively obtain a change of an amount of hemoglobin accompanied by a brain activity, i.e., a change of a blood flow amount or an activation state of oxygen metabolism. In the optical measurement, a brain activity is measured every measurement point (measurement channel) configured by a pair of the light transmitting probe 4a and the light receiving probe 4b.

Figure 2:
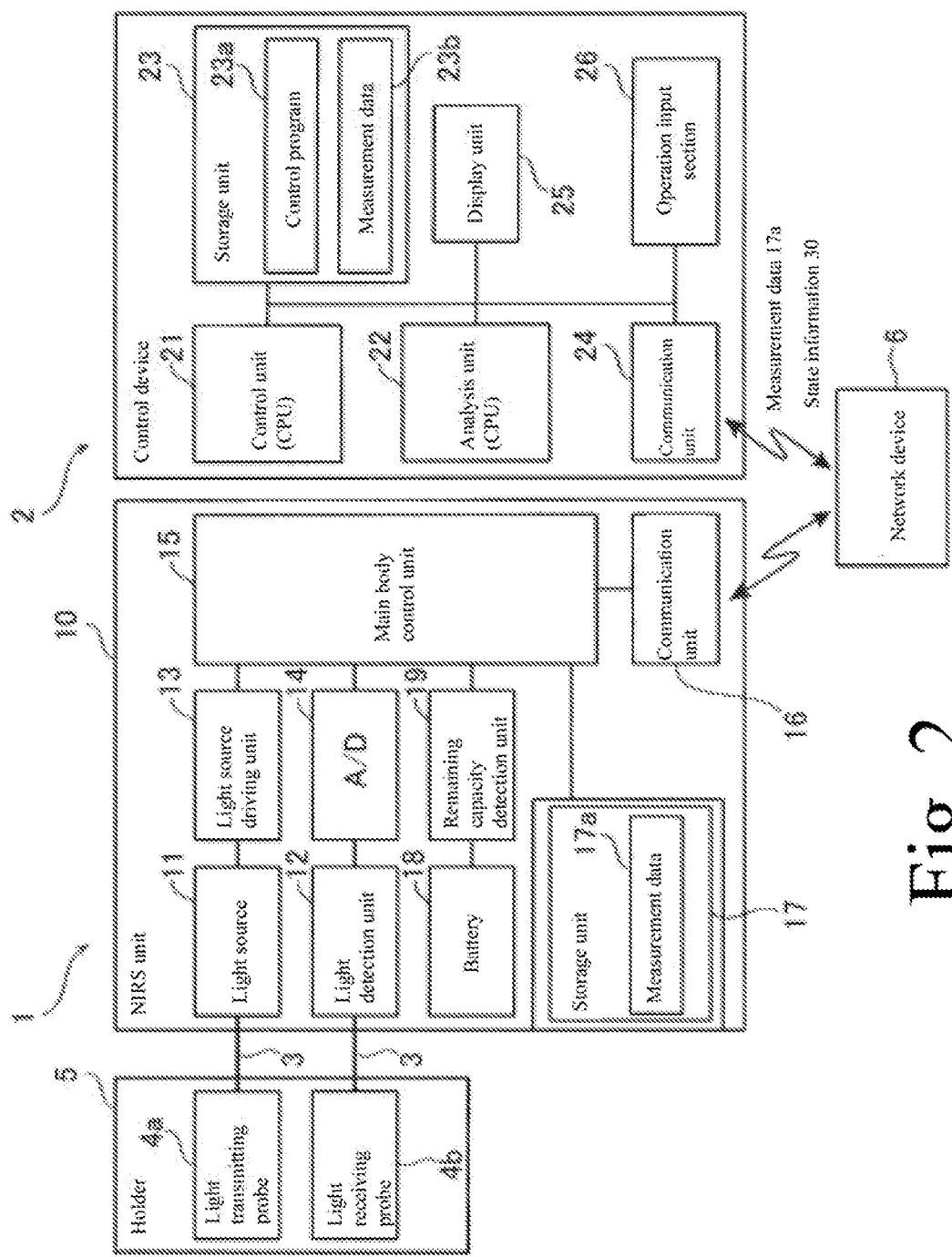
FIG. 2 is a block diagram showing a configuration of an optical measurement unit and a control device of the optical measurement system.

As shown in FIG. 2, the optical measurement unit 1 is equipped with a light source 11, a light detection unit 12, a light source driving unit 13, an A/D converter 14, a main body control unit 15, a communication unit 16, and a storage unit 17 in a housing 10 having a portable size. Further, the optical measurement unit 1 is equipped with a battery 18 and a remaining capacity detection unit 19.

The light source 11 is configured to output measurement light to the light transmitting probe 4a via the optical fiber 3. The light source 11 is comprised of, e.g., a semiconductor laser or an LED capable of outputting measurement lights of a plurality of wavelengths in a wavelength region of rear-infrared light. The light detection unit 12 is comprised of, e.g., an APD (Avalanche photodiode) or a photomultiplier tube, and is configured to detect the measurement light incident to the light receiving probe 4b via the optical fiber 3. As a result, the light detection unit 12 outputs a received light quantity signal corresponding to the detected measurement light. The light source driving unit 13 is configured to turn on and off the light source 11 in accordance with the control signal from the main body control unit 15. The A/D converter 14 is configured to convert the received light quantity signal of the light detection unit 12 into a predetermined digital signal and output the digital signal to the main body control unit 15. The main body control unit 15 performs operation controls of the light source 11 (light source driving unit 13) and the light detection unit 12 in accordance with the measurement conditions, such as, e.g., the set sampling period and the number of measurement channels, and the measurement parameters on the output intensity of the measurement light and the detection sensitivity of the light detection unit 12.

The main body control unit 15 is a computer composed of a CPU, a memory, etc., and is configured to control each portion of the aforementioned optical measurement unit 1. With this, the main body control unit 15 performs controls of storing the measurement data to the storage unit 17 based on the obtained received light quantity signal, transmission of the measurement data to the control device 2, etc.

The communication unit 16 is comprised of a wireless communication module, and can perform a wireless communication between this communication unit 16 and a later-described communication unit 24 of the control device 2. The storage unit 17 is comprised of a non-volatile memory, such as, e.g., a flash memory. Further, the storage unit 17 is comprised of a portable storage medium detachably attached to the optical measurement unit 1. Therefore, in cases where, for example, the remaining memory capacity (the remaining amount of the storage capacity) of the storage unit 17 becomes low, it is possible to secure a remaining memory capacity by exchanging storage mediums. In the storage unit 17, measurement data 17a of the brain function measurement, etc., are stored. The optical measurement unit 1 can transmit the measurement data 17a to the control device 2 by the communication unit 16 in real time, and also can store the measurement data 17a in the storage unit 17.

The power supply to each portion of the optical measurement unit 1 is performed by a battery 18. Other than this, the optical measurement unit 1 can receive a power supply in a wired manner by connecting a power cable not illustrated to the optical measurement unit 1. The remaining capacity detection unit 19 has a function of detecting the remaining battery capacity of the battery 18. The remaining capacity detection unit 19 detects, for example, the terminal voltage of the battery 18 to detect the remaining battery capacity by a voltage measurement method that obtains the remaining battery capacity based on the detected voltage value.

Next, as shown in FIG. 2, the control device 2 is a computer (PC) equipped with a control unit 21 comprised of, e.g., a CPU, an analysis unit 22, a storage unit 23 composed of, e.g., an HDD, and a communication unit 24 comprised of a wireless communication module (or an externally connected wireless communication unit). The control unit 21 and the analysis unit 22 are each configured as a function block which is realized by executing the control program 23a stored in the storage unit 23 by the CPU. It should be noted that the control unit 21 and the analysis unit 22 may be configured not by a function block but by a dedicated hardware (dedicated CPU). The control device 2 is further equipped with a display unit 25 comprised of, e.g., a liquid crystal display, and an operation input section 26 comprised of, e.g., a keyboard and a mouse.

Each part of the control device 2 is controlled by the control unit 21. The control unit 21 is configured to store the measurement data 17a of the optical measurement unit 1 via the communication unit 24 and stored it in the storage unit 23. The analysis unit 22 performs arithmetic processing for executing imaging (graphing) processing, statistical processing, etc., with respect to the measurement data 23b stored in the storage unit 23. In the first embodiment, the control unit 21 is configured to control a plurality of optical measurement units 1 so that a simultaneous measurement is performed by a part or the entirety of the plurality of optical measurement units 1.

The storage unit 23 stores a control program 23a and various information, such as, e.g., measurement conditions and parameters. Further, the storage unit 23 is configured to store measurement data 17a of a plurality of brain functions obtained from respective optical measurement units 1 as measurement data 23b. Further, the communication unit 24 is configured to perform information transfer of measurement conditions, measurement parameters, measurement data, etc., by the intercommunication between the communication unit 24 and the communication unit 16 of each optical measurement unit 1.

Figure 3:
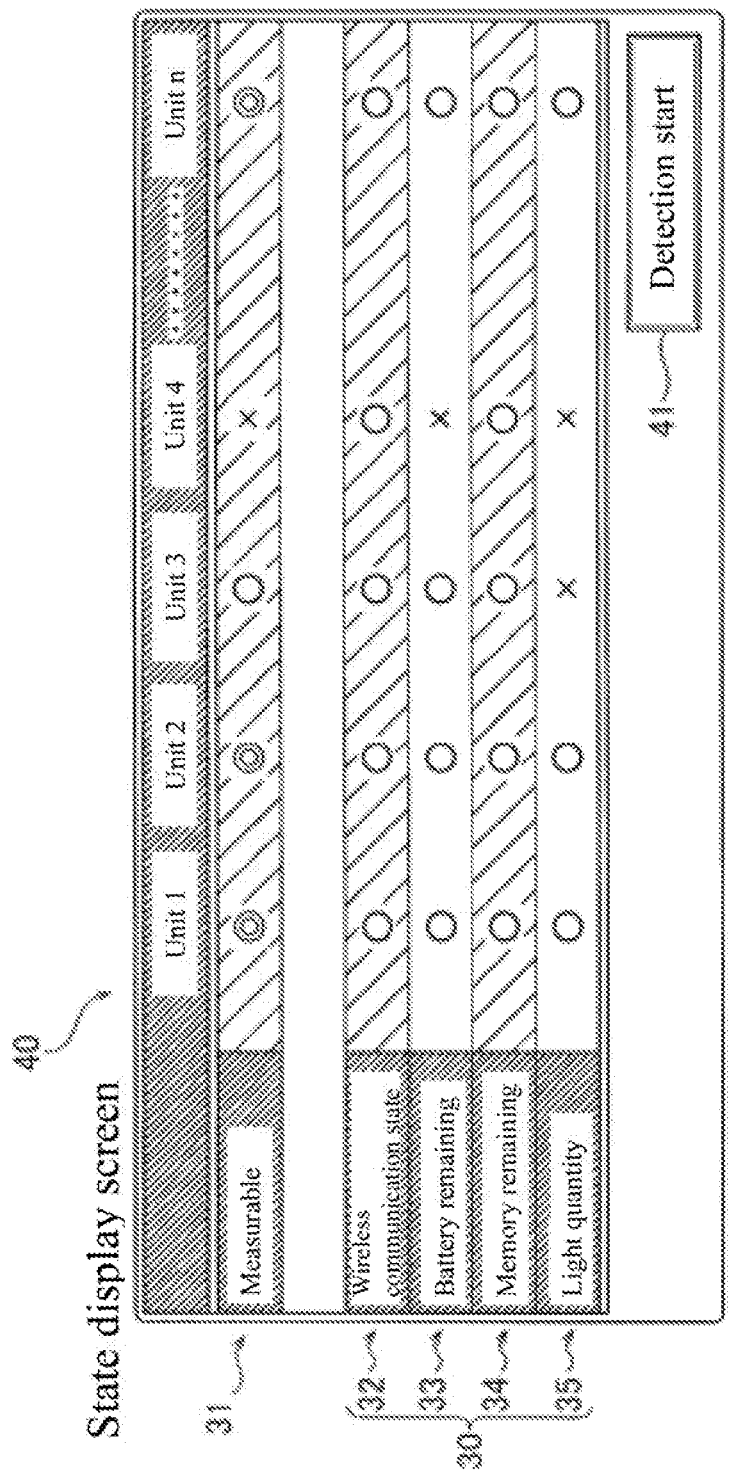
FIG. 3 is a view showing a state display screen of the optical measurement system according to the first embodiment of the present invention.

In the first embodiment, as shown in FIG. 3, the communication unit 24 is configured to obtain specific state information 30 on whether or not the optical measurement unit 1 is in a measurable state via a wireless communication for each of the plurality of optical measurement units 1. The state information 30 obtained on each of the plurality of optical measurement units 1 is collectively displayed on a state display screen 40 of the display unit 25. At this time, the control unit 21 is configured to, based on state information 30, specify optical measurement units 1 capable of performing a simultaneous measurement and collectively display the information on whether or not a simultaneous measurement is possible (measurement availability information 31) on the display unit 25.

Specifically, the control unit 21 makes the display unit 25 display in window a state display screen 40. The state display screen 40 includes state information 30 composed of four items and measurement availability information 31 on whether or not a simultaneous measurement is available for each of the optical measurement units 1 from 1 to n. In FIG. 3, an example in which whether or not it is good or bad on each of the information is listed in a ○/× format is shown. The control unit 21 is configured to obtain the state information 30 of each optical measurement unit 1 at certain time intervals and update the state display screen 40 regularly. Further, the control unit 21 is configured to obtain the state information 30 of each optical measurement unit 1 and update the state display screen 40 even when a detection start button 41 on the state display screen 40 is operated via the operation input section 26 (see FIG. 2).

In the first embodiment, the state information 30 includes the information 32 on communication state (column of "wireless communication state") between the optical measurement unit 1 and the control device 2, and the information 33 on the remaining battery capacity of the optical measurement unit 1. Further, the state information 30 further includes the information 34 on the remaining memory capacity of the optical measurement unit 1 and the received light quantity signal information (column of "light quantity") 35 of the optical measurement unit 1.

The information 32 on the communication state between the optical measurement unit 1 and the control device 2 is information showing the communication strength between the optical measurement unit 1 and the control device 2. For example, as shown in FIG. 2, in cases where the optical measurement unit 1 and the control device 2 communicate via the network device 6, such as a router, the control unit 21 transmits a command for obtaining the communication strength between each optical measurement unit 1 and the network device 6 to the network device 6. The communication strength is obtained as a response from the network device 6 to the command. Further, in cases where the optical measurement unit 1 and the control unit 2 perform a wireless communication not via the network device 6, it may be configured such that the communication unit 24 directly detects the communication strength. The control unit 21 judges whether or not the obtained communication strength is equal to or above a predetermined level sufficient to perform a transmission of the measurement data 17*a*, and makes the display unit 25 display the judged result. In FIG. 3, a display example is shown in which when the signal strength is equal to or more than a predetermined level, it is shown as "○", and when the signal strength is less than the predetermined level, it is shown as "×".

The information 33 of the remaining battery capacity of the optical measurement unit 1 is obtained as a detection result of the remaining capacity detection unit 19 of each optical measurement unit 1. The control unit 21 judges whether or not the remaining battery capacity obtained via the communication unit 24 is equal to or more than a predetermined value (for example, 50%), and makes the display unit 25 display the judged result. In FIG. 3, a display example is shown in which when the remaining battery capacity is equal to or more than a predetermined value, it is shown as "○", and when the remaining battery capacity is less than the predetermined value, it is shown as "×".

The information 34 of the remaining memory capacity of the optical measurement unit 1 is a remaining memory capacity for the measurement data 17*a* of the storage unit 17 of each optical measurement unit 1. The control unit 21 inquires the remaining memory capacity to each optical measurement unit 1 via the communication unit 24 and obtains the remaining memory capacity by making the main body control unit 15 of each optical measurement unit 1 refer the storage unit 17. The control unit 21 judges whether or not the remaining memory capacity obtained via the communication unit 24 is equal to or more than a predetermined value, and makes the display unit 25 display the judged result. In FIG. 3, a display example is shown in which when the remaining memory capacity is equal to or more than a predetermined value, it is shown as "○", and when the remaining memory capacity is less than the predetermined value, it is shown as "×".

The control unit 21 determines the data amount (unit data amount) of the measurement data 17*a* per unit time based on the set measurement conditions (sampling period, the number of measurement channels, etc.). The predetermined value of the remaining memory capacity is set as a free data amount corresponding to a predetermined time period by a determined unit data amount (for example, 1 hour). Other than the above, for example, in cases where the measurement time from the measurement start to the measurement completion is set in advance, the predetermined value is set as a free data amount corresponding to a set measurement time.

The received light quantity information 35 of the optical measurement unit 1 is information on the received light quantity signal level of the light detection unit 12 to the measurement light from the light source 11 of the optical measurement unit 1. The received light quantity information 35 is obtained by actually irradiating measurement light from the light source 11 and obtain the received light quantity signal of the light detection unit 12. The control unit 21 judges whether or not the received light quantity signal level obtained via the communication unit 24 is within a predetermined range preferable for a measurement, and makes the display unit 25 display the judged result. In FIG. 3, a display example is shown in which when the received light quantity is within a predetermined range, it is shown as "○", and when the received light quantity is outside the predetermined value, it is shown as "×".

For example, in cases where the mounting state of the holder 5 to a subject P is poor and therefore the probes (light transmitting probes 4*a* and light receiving probes 4*b*) are not in contact with the head surface of the subject P, or in cases where hair, etc., is interposed between the head surface and the prove so that the measurement light is interrupted, a normal light receipt signal cannot be obtained, and the received light quantity information 35 is shown as "×". In such a case, after the re-mounting of the holder 5 and/or the probe, an adjustment (calibration) of the light-receiving sensitivity of the light detection unit 12 is performed. When the received light quantity re-obtained as the adjustment result falls within a predetermined range, the received light quantity information 35 is shown as "○".

The control unit 21 generates measurement availability information 31 based on the state information 30 of these four items. In the first embodiment, when all of the four items are shown as "○", the measurement availability information 31 is shown as "⊙". In cases where either the communication state or the remaining battery capacity is shown as "×", the measurement availability information 31 is shown as "×". "X" shows the state in which a simultaneous measurement cannot be performed. Further, in cases where the communication state and the remaining battery capacity are both shown as "○" and either the remaining memory capacity or the light quantity is shown as "×", it is shown as "○". This indicates a state with conditions in which it is recommended to make all items set to be shown as "○" to improve the data quality of the measurement data 17*a* although a simultaneous measurement can be performed.

Figure 4:
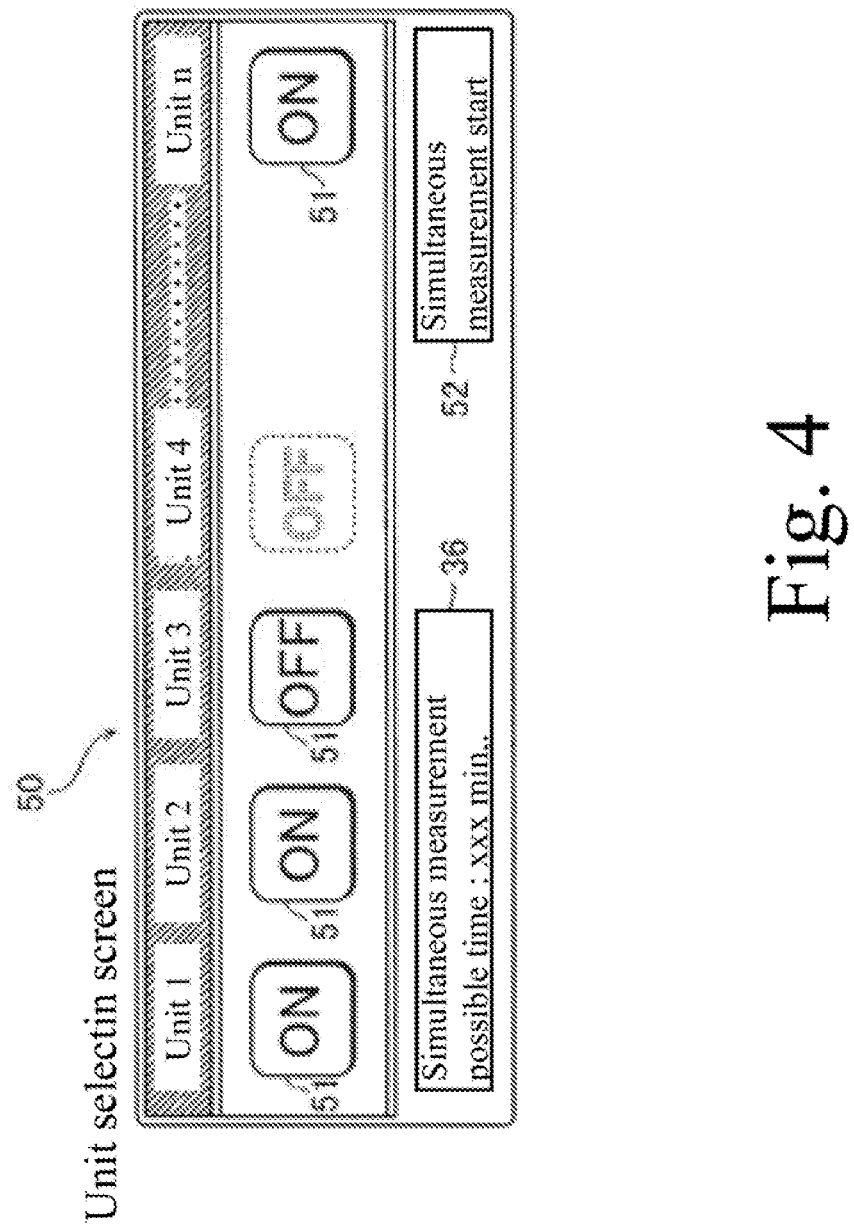
FIG. 4 is a view showing a unit selection screen of the optical measurement system according to the first embodiment of the present invention.

In addition to the aforementioned state display screen 40, as shown in FIG. 4, the control unit 21 is configured to make the display unit 25 show in window a unit selection screen 50. In the unit selection screen 50, the control unit 21 is configured to make the display unit 25 display optical measurement units 1 that can perform a simultaneous measurement in a selectable manner. Further, the control unit 21 is configured to calculate each measurement possible time of the optical measurement units 1 based on the remaining batter capacity and the remaining memory capacity. The control unit 21 is configured to calculate a simultaneous measurement possible time 36 when a simultaneous measurement is performed by a plurality of optical measurement units 1 based on respective measurement possible times of the plurality of optical measurement units 1 and display it on the unit selection screen 50 of the display unit 25.

The unit selection screen 50 includes select display buttons 51 showing whether or not a simultaneous measurement is to be performed (ON or OFF) for each of the optical measurement units 1 from 1 to n. With this selection display buttons 51, the operation input section 26 is configured such that an individual selection operation can be accepted on the optical measurement unit 1 that can perform a simultaneous measurement. The control unit 21 displays so that the select display button 51 can be selected (turned ON or OFF) for the optical measurement unit 1 in which it is displayed that a simultaneous measurement can be performed (shown as "○") for the measurement availability information 31 (see FIG. 3) of the state display screen 40. On the other hand, the control unit 21 makes non-selectable by graying out (in FIG. 4, it is shown by a broken line) the select display button 51 for the optical measurement unit 1 that was displayed to be unavailable to perform a simultaneous measurement (shown as "×") on the measurement availability information 31.

The simultaneous measurement possible time 36 is calculated based on the measurement possible time of each optical measurement unit 1. For this reason, the control unit 21 calculates the measurement possible time of the optical measurement unit 1 every unit. The measurement possible time includes a measurement possible time based on the remaining battery capacity and a measurement possible time based on the remaining memory capacity.

The measurement possible time based on the remaining battery capacity is calculated as a value obtained by, for example, dividing the remaining battery capacity of the optical measurement unit 1 by a previously set power consumption (unit power consumption) per unit time. The measurement possible time based on the remaining memory capacity is calculated as a value obtained by, for example, dividing the remaining memory capacity of the optical measurement unit 1 by a data amount (unit data amount) per unit time under measurement conditions set by a user. The control unit 21 employs a smaller value between a value of the measurement possible time based on the remaining battery capacity and a value of the measurement possible time based on the remaining memory capacity as a measurement possible time of each optical measurement unit 1. The control unit 21 is configured such that the smallest value among the measurement possible times of each optical measurement unit 1 is calculated as a simultaneous measurement possible time 36.

When an optical measurement unit 1 is selected on the unit selection screen 50, the control unit 21 recalculates the simultaneous measurement possible time 36 considering the measurement possible time of the selected optical measurement unit 1 and updates simultaneous measurement possible time. In the same manner, when a selection of an optical measurement unit 1 is released, the control unit 21 recalculates the simultaneous measurement possible time 36 excluding the measurement possible time of the selection released optical measurement unit 1 and updates the simultaneous measurement possible time. Further, the control unit 21 is configured to initiate a simultaneous measurement by the selected optical measurement unit 1 when the simultaneous measurement start button 52 of the unit selection screen 50 is operated via an operation input section 26.

Figure 5:
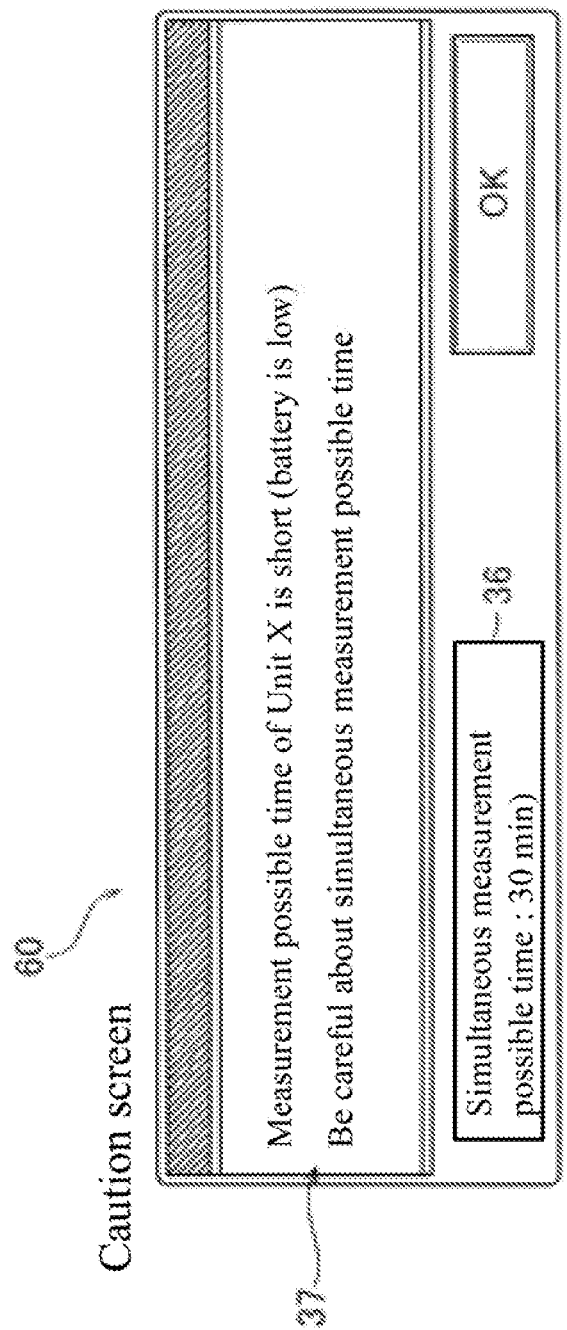
FIG. 5 is a view showing a caution screen of the optical measurement system according to the first embodiment of the present invention.

In the first embodiment, the control unit 21 is configured to obtain each state information 30 of optical measurement units 1 during the measurement operation and calculate each of the measurement possible time and the simultaneous measurement possible time 36, even after the start of simultaneous measurements. Further, as shown in FIG. 5, the control unit 21 is configured to make the display unit 25 display in window a caution screen 60 when there is an optical measurement unit 1 in which the calculated measurement possible time became smaller (fewer) than a predetermined value (for example, 30 minutes).

In the caution screen 60, the control unit 21 is configured to make the display unit 25 display the information (message 37) showing that the calculated measurement possible time has become smaller (fewer) than a predetermined value. That is, the caution screen 60 includes a message 37 indicating that the measurement possible time has become short by specifying the optical measurement unit 1 (Unit X in FIG. 5). The message 37 includes causes of shortening the measurement possible time (insufficient remaining battery capacity, or insufficient remaining memory capacity).

A user who confirmed the caution screen 60, in the case of insufficient remaining battery capacity, can deal with by, for example, connecting a power cable to the specified optical measurement unit 1. In cases where no power source is available nearby or the remaining memory capacity is insufficient, a user can take some actions, such as, e.g., changing the implementation plan of the measurement to once terminate the simultaneous measurement. Even in this case, unlike a case in which the measurement of the optical measurement unit 1 suddenly stops, it is possible to terminate the measurement at an appropriate timing so that the measurement can be easily resumed.

By the configuration described above, in the optical measurement system 100, in performing a simultaneous measurement, the state information 30 and the measurement availability information 31 on each of the plurality of optical measurement units 1 are collectively displayed on the state display screen 40 of the display unit 25. Further, in the optical measurement system 100, optical measurement units 1 capable of performing a simultaneous measurement are displayed on the unit selection screen 50 of the display unit 25 in a selectable manner, and individual selection operations can be accepted via the operation input section 26. By the plurality of optical measurement units 1 (a part or all of Unit 1 to Unit n) selected as described above, a simultaneous measurement of brain function measurements of a plurality of subjects P is performed.

Next, with reference to FIGS. 3 to 7, the control processing of the brain function measurement of the optical measurement system 100 of the first embodiment will be described. As described above, the control processing of the optical measurement unit 1 is executed by the main body control unit 15, and the control processing of the control device 2 is executed by the control unit 21.

Figure 6:
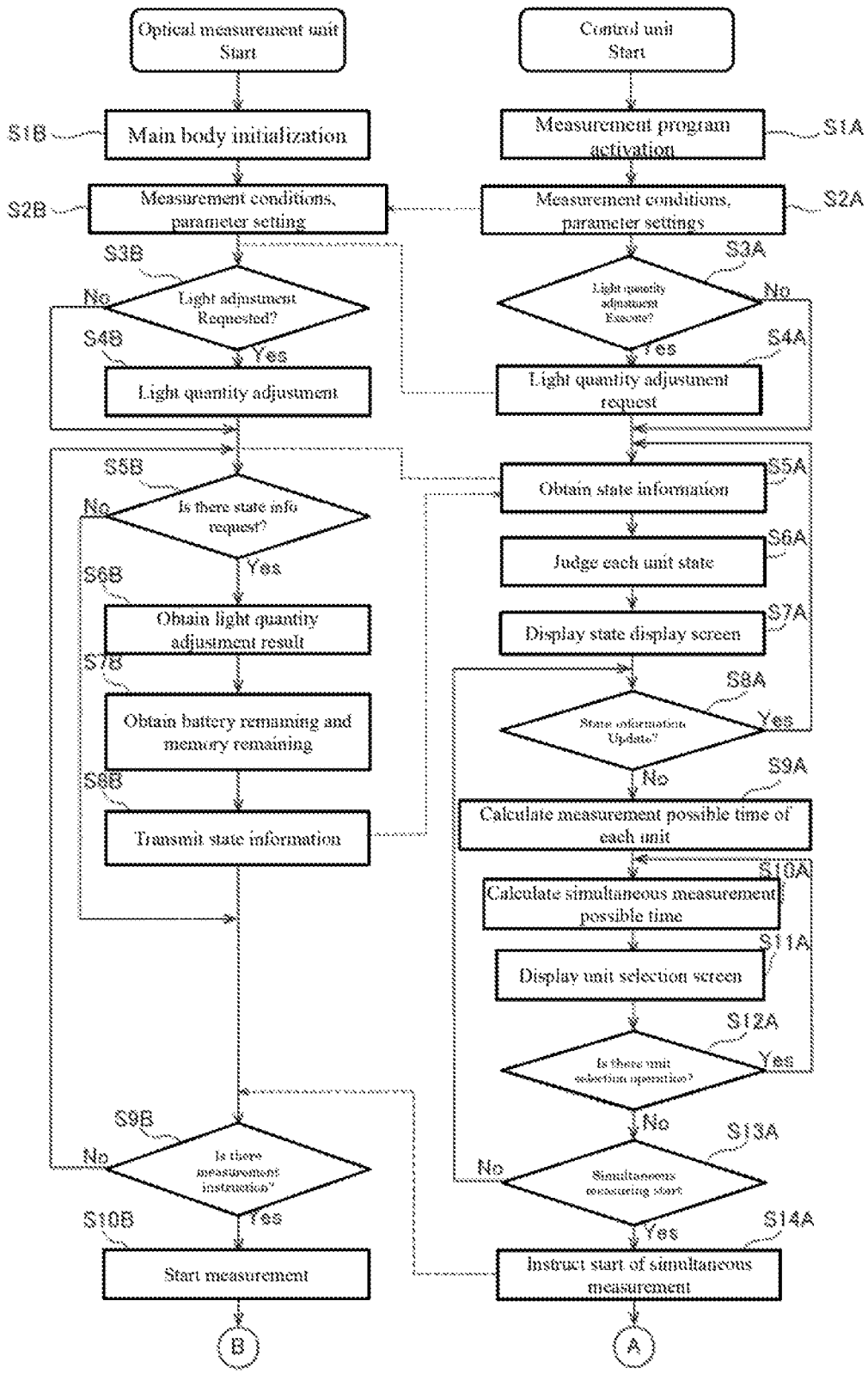
FIG. 6 is a flowchart (first half) for explaining an operation of a simultaneous measurement of the optical measurement system according to the first embodiment of the present invention.

Initially, the processing on the control device 2 side will be described. As shown in FIG. 6, on the control device 2 side, in Step S1A, a measurement program is activated (executed) by the control unit 21. Next, in Step S2A, the control unit 21 sets measurement conditions and measurement parameters of the brain function measurement in accordance with an input operation by a user or data reading. Further, the control device 2 transmits the set measurement conditions and measurement parameters to each optical measurement unit 1.

In Step S3A, the control unit 21 judges whether or not an adjustment (calibration) of the light quantity (detection sensitivity of the light detection unit 12) of the optical measurement unit 1 should be performed. In the case of performing the light quantity adjustment, in Step S4A, a light quantity adjustment request is transmitted to the optical measurement unit 1. The light quantity adjustment is executed to a non-executed optical measurement unit 1 after the activation, and also executed based on an input operation by a user when, for example, the mounting condition of the holder 5 to the subject P is corrected.

Next, in Step S5A on the control device 2 side, the control unit 21 executes obtain processing of the state information 30. The control unit 21 transmits an instruction for requesting the state information 30 to each optical measurement unit 1 by the communication unit 24. As a result, the control device 2 obtains the state information 30 from each of the plurality of optical measurement units 1. As to the information 32 of the communication state, the control unit 21 obtains from the network device 6 or the communication unit 24.

When the control device 2 obtains the state information 30, in Step S6A, the control unit 21 performs a state judgement of each optical measurement unit 1 based on the obtained state information 30. That is, the control unit 21 judges each item of the information 32 of the communication state, the information 33 of the remaining battery capacity, the information 34 of the remaining memory capacity, and the receiving light quantity information 35 shown in FIG. 3 in accordance with judgement conditions. Further, the control unit 21 generates measurement availability information 31 on whether or not a simultaneous measurement can be performed based on the judgement result every optical measurement unit 1.

Next, in Step S7A, the control unit 21 makes the display unit 25 display the state display screen 40 in which the state information 30 and the measurement availability information 31 are collectively displayed.

Next, in Step S8A, the control unit 21 judges whether or not the state information 30 should be updated. Specifically, in cases where a predetermined time has passed since the state information 30 was obtained, or in cases where an input of the detection start button 41 (see FIG. 3) on the state display screen 40 is accepted, the control unit 21 updates the state information 30. When updating the state information 30, the processing returns to Step S5A, the state information 30 is again requested to each optical measurement unit 1, and the state information 30 is updated in Step S7A.

In the case of not updating the state information 30, the control unit 21 calculates the measurement possible time of each optical measurement unit 1 in Step S9A. The control unit 21 calculates the measurement possible time every unit based on the unit power consumption, the unit data amount, the remaining battery capacity, and the remaining memory capacity of the state information 30.

Next, in Step S10A, the control unit 21 calculates the simultaneous measurement possible time 36. That is, the control unit 21 obtains the smallest value among the measurement possible times of each optical measurement unit 1 calculated in Step S9A as a simultaneous measurement possible time 36. In Step S11A, the control unit 21 make the display unit 25 display the unit selection screen 50 including the select display button 51 of each optical measurement unit 1 and the simultaneous measurement possible time 36.

Next, the control unit 21 judges in Step S12A whether or not a unit selection operation by a user is accepted. When any one of select display buttons 51 of the optical measurement unit 1 is turned ON or OFF, Step S10A and Step S11A are executed again. With this, the user's unit selection operation is reflected on the unit selection screen 50, and the unit selection screen 50 is updated so that the simultaneous measurement possible time 36 at the optical measurement unit 1 after the selection is displayed.

In the case of no unit selection operation, the control unit 21 judges in Step S13A whether or not a simultaneous measurement initiation operation by a user is accepted. When the simultaneous measurement start button 52 (see FIG. 4) is not operated by a user, the processing returns to Step S8A. Therefore, as a result that Step S8A (S5A to S8A) to Step S13A will be repeated, the state display screen 40 and the unit selection screen 50 are updated in accordance with the operation by a user or the progress of the measurement preparation operation.

When the input of the simultaneous measurement start button 52 is accepted in Step S13A, the control unit 21 transmits an instruction to initiate the simultaneous measurement to each selected optical measurement unit 1 in Step S14A. As a result, on the selected optical measurement unit 1 side, brain function measurements are initiated simultaneously.

When brain function measurements are initiated, in each optical measurement unit 1, measurement data 17a is generated with time. Depending on the previously set measurement mode, the measurement data 17a is stored in the storage unit 17 of each optical measurement unit 1 or transmitted to the control device in real time. Even in a mode that the measurement data 17a is transmitted to the control device 2, when the communication state is not good and a sufficient transmission speed cannot be obtained, the measurement data 17a is stored (buffered) in the storage unit 17 temporality.

Figure 7:
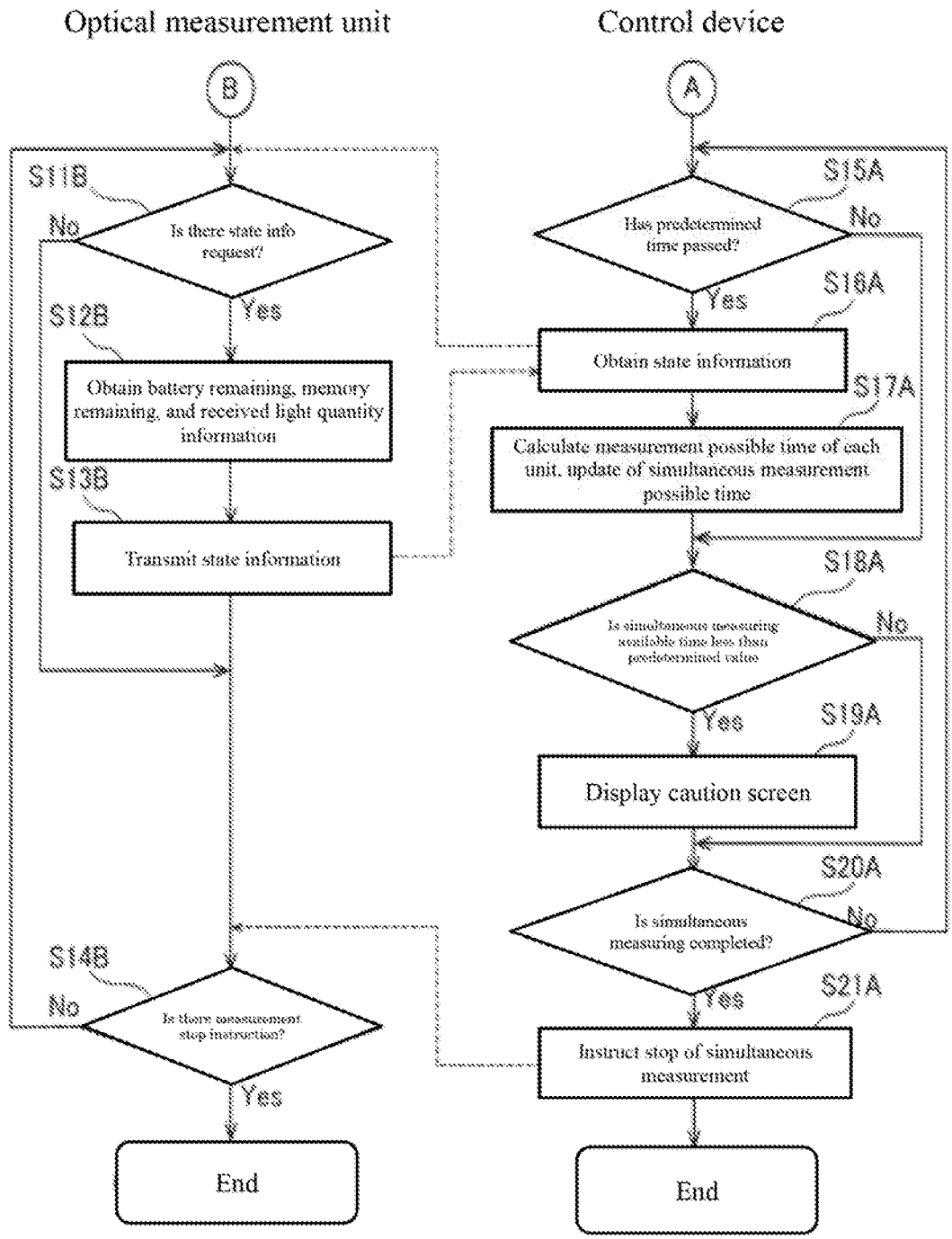
FIG. 7 is a latter half of the flowchart shown FIG. 6.

After the initiation of the simultaneous measurement, in Step S15A in FIG. 7, the control unit 21 judges whether or not a predetermined time has passed. When the predetermined time has not passed, the processing proceeds to Step S18A. When the predetermined time has passed, in Step S16A, the control unit 21 executes obtain processing of the state information 30. The contents of the processing are the same as in the aforementioned Step S5A.

Next, in Step S17A, based on the received state information 30, the control unit 21 calculates a latest value of the measurement possible time of each optical measurement unit 1 during the measurement operation and updates it. Further, the control unit 21 updates the simultaneous measurement possible time 36 based on the latest value of the obtained measurement possible time.

Then, in Step S18A, the control unit 21 judges whether or not the simultaneous measurement possible time 36 is less than the predetermined value. When the simultaneous measurement possible time is equal to or larger than the predetermined value, the processing advances to Step S20A.

When the simultaneous measurement possible time is less than the predetermined value, the control unit 21 makes the display unit 25 display the caution screen 60 in Step S19A. The control unit 21 makes the display unit 25 display a message 37 specifying an optical measurement unit 1 (Unit X) shortest in measurement possible time together with the simultaneous measurement possible time 36.

Next, in Step S20A, the control unit 21 judges whether or not the simultaneous measurement should be terminated. When the simultaneous measurement possible time is not to be terminated, the processing returns to Step S15A. As a result, during the simultaneous measurement, the processing of Step S15A to Step S20A will be repeated, and therefore the simultaneous measurement possible time 36 (measurement possible time of each optical measurement unit 1) is monitored.

On the other hand, when it has reached the previously set measurement time or when the measurement termination is accepted by the user's operation input, in Step S21A, the control unit 21 transmits an instruction to terminate the simultaneous measurement to each optical measurement unit 1, and terminates the simultaneous measurement processing.

Next, the optical measurement unit 1 side processing will be described.

As shown in FIG. 6, on the optical measurement unit 1 side, in Step S1B, initialization of each part is performed by the main body control unit 15. In Step S2B, the main body control unit 15 sets measurement conditions and measurement parameters of the brain function measurements received from the control device 2.

In Step S3B, the main body control unit 15 judges whether or not there exists a light quantity adjustment request. When there is a light quantity adjustment request, in Step S4B, a light quantity adjustment is performed. As a result, the received light quantity information 35 as an adjustment result is stored in the storage unit 17.

Next, in Step S5B, the main body control unit 15 judges whether or not there exists a request of the state information 30. When a request of the state information 30 is received, in Step S6B, the main body control unit 15 obtains the received light quantity signal information as a result of a light quantity adjustment in Step S4B from the storage unit 17. Sequentially, in Step S7B, the main body control unit 15 obtains the remaining battery capacity from the remaining capacity detection unit 19, and obtains the remaining memory capacity by referring to the storage unit 17. Next, in Step S8B, the main body control unit 15 transmits the obtained state information 30 (received light quantity signal information, the remaining battery capacity, and the remaining memory capacity) to the control device 2.

Further, when a request of the state information 30 is not received in Step S5B, the main body control unit 15 judges whether or not a measurement start instruction is received in Step S9B. When a measurement start instruction is not received, the processing is returned to Step S5B. Therefore, each optical measurement unit 1 waits by repeating Step S5B to Step S9B until a measurement start instruction is received.

Further, when it is judged that there is a measurement start instruction in Step S9B, the main body control unit 15 starts the brain function measurement in Step S10B. Thereafter, obtaining of measurement data 17*a* is continued until a measurement stop instruction is received.

After the start of the brain function measurement, in Step S11B in FIG. 7, the main body control unit 15 judges whether or not a request of the state information 30 is received. When a request of the state information 30 is received, in Step S12B, the main body control unit 15 obtains the information 33 on the remaining battery capacity, the information 34 on the remaining memory capacity, and the receiving light quantity information 35, and transmits the state information 30 to the control device 1 in Step S13B. In this case, the received light quantity information 35 is obtained based on the light receipt signal of the light detection unit 12 under the measurement operation.

Further, when a request of the state information 30 is not received in Step S11B, the main body control unit 15 judges whether or not a measurement should be stopped in Step S14B. When a measurement stop instruction is not received, the processing is returned to Step S11B. Therefore, each optical measurement unit 1 repeats the processing of Step S11B to Step S14B while continuing the measurement operation until a measurement stop instruction is received.

When an instruction of a simultaneous measurement stop is received in Step S14B, the main body control unit 15 terminates the measurement processing. With the above, the measurement processing operation of the optical measurement system 100 is completed.

In the first embodiment, the following effects can be obtained.

In the first embodiment, as described above, the communication unit 24 that obtains the specific state information 30 on whether the optical measurement unit 1 is in a measurable state by communication for each of a plurality of optical measurement units 1 and the display unit 25 that collectively displays the obtained state information 30 for each of the plurality of optical measurement units 1 are mounted on the control device 2. With this, a user can collectively confirm whether or not each optical measurement unit 1 is in a measurable state from the state information 30 displayed by the display unit 25 of the control device 2. As a result, the user can quickly grasp the optical measurement unit 1 which is not in a measurable state, and operations for making it in a measurable state can be performed. Further, it is also possible to collectively grasp measurable optical measurement units 1, and therefore as to the measurable optical measurement units 1, the preparation for the brain function measurement can be completed quickly. From the above, according to the optical measurement system 100 of the first embodiment, when performing a simultaneous measurement by a plurality of optical measurement units 1, it is possible to shorten the time required for the measurement preparation by facilitating the grasping of the state of each optical measurement unit 1.

Further, in the first embodiment, as described above, the control unit 21 of the control device 2 is configured such that the measurement availability information 31 on whether or not it is possible to perform a simultaneous measurement is collectively displayed for each of the plurality of optical measurement unit 1. With this, it is possible to grasp whether or not each of the plurality of optical measurement units 1 can perform a simultaneous measurement by the state display screen 40 of the display unit 25 at a glance. Further, by just looking at the display (measurement availability information 31) of the display unit 25, it is possible to immediately distinguish between a unit which can perform a simultaneous measurement and a unit which cannot perform a simultaneous measurement. As s result, it is possible to further facilitate grasping of the state of each optical measurement unit 1, and also possible to improve the convenience for a user.

Further, in the first embodiment, as described above, the operation input section 26 that accepts an individual selection operation is provided in the optical measurement unit 1 which can performs a simultaneous measurement. Further, the control unit 21 of the control device 2 is configured such that the simultaneous measurement is performed by the selected optical measurement units 1. With this, in cases where, for example, only some of the plurality of optical measurement units are used, it is possible for a user to start the brain function measurements only by selecting the optical measurement units 1 which can perform a simultaneous measurement. As a result, it is possible to further shorten the measurement preparation time.

Further, in the first embodiment, as described above, the state information 30 includes the information 32 on communication state and the information 33 on the remaining battery capacity of the optical measurement unit 1. With this, a user can collectively grasp the information 32 on the communication state required to make the optical measurement unit 1 execute the measurement operation and the information 33 of the remaining battery capacity on each optical measurement unit 1. As s result, it becomes possible to easily and quickly grasp the information required to make each optical measurement unit 1 in a measurable state.

Further, in the first embodiment, as described above, the state information 30 includes the information 34 on the remaining memory capacity and the information 35 on the received light quantity information 35. With this, it is possible to collectively grasp whether or not the remaining capacity for continuously measuring by each optical measurement unit 1 is secured by the information 34 of the remaining memory capacity. Further, by the received light quantity information 35, it is possible to collectively grasp the good or bad mounting state of the light transmitting probe 4*a*, the light receiving probe 4*b*, or the holder 5 to a subject, or the necessity of a sensitivity adjustment (calibration) of the light detection unit 12 of each optical measurement unit 1. As a result, it becomes possible to grasp the information required to obtain an excellent measurement data 17*a* by each optical measurement unit 1.

Further, in the first embodiment, as described above, the control unit 21 of the control device 2 is configured to calculate a simultaneous measurement possible time 36 when a simultaneous measurement is performed by a plurality of optical measurement units 1 based on respective measurement possible times of the plurality of optical measurement units 1 and display the simultaneous measurement possible time 36 on the display unit 25. With this, it is possible for a user to easily judge whether or not it is possible to perform a simultaneous measurement along the user's execution plan based on the simultaneous measurement possible time 36. When the simultaneous measurement possible time 36 is insufficient, a user can take an action of changing a battery of the optical measurement unit 1 in which the remaining battery capacity remains to some degrees or changing the execution plan of the measurements. With this, it is possible to further improve the convenience to the user.

Further, in the first embodiment, as described above, the control unit 21 of the control device 2 is configured to obtain each state information 30 of optical measurement units 1 during the measurement operation and display the information (message 37) showing the optical measurement unit 1 in which the measurement possible time has become less than the predetermined value on the display unit 25. With this, even in cases where the simultaneous measurement by a plurality of optical measurement units 1 is being executed, when the measurement possible time of the optical measurement unit 1 has become short, the user can grasp the optical measurement unit 1. With this, it is possible to take actions, such as, e.g., an action of connecting a power cable to the unit in which the measurement possible time has become short and an action of changing the execution plan of the measurement to perform a measurement interruption at an appropriate timing.

Second Embodiment

Next, with reference to FIG. 8, an optical measurement system according to the second embodiment of the present invention will be described. In the second embodiment, unlike the first embodiment equipped with a single control device 2, an optical measurement system 200 equipped with a plurality of control devices 102 will be explained. In the second embodiment, as to the same configuration as the first embodiment, the same symbol is allotted and the explanation will be omitted.

Figure 8:
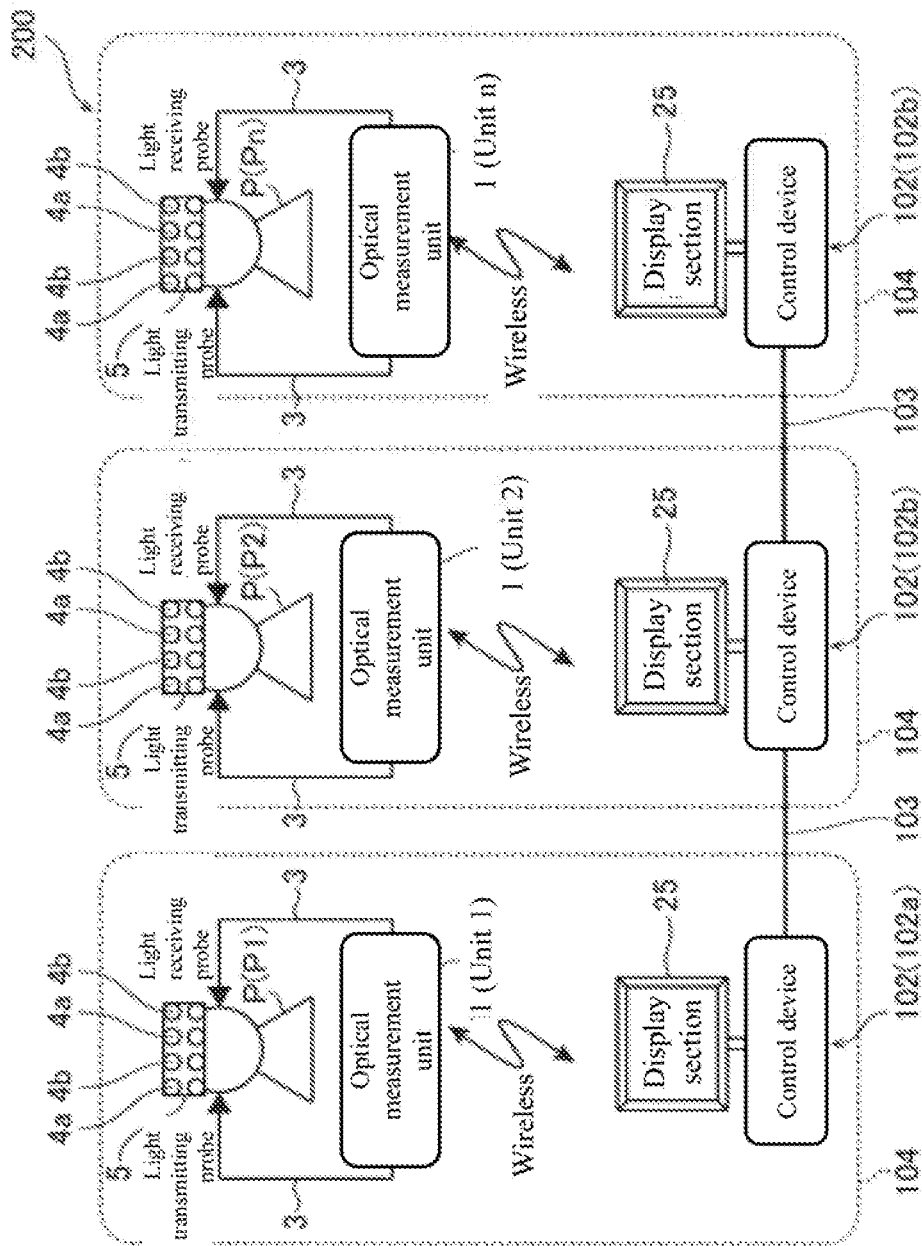
FIG. 8 is a schematic view showing an entire configuration of an optical measurement system according to a second embodiment of the present invention.

As shown in FIG. 8, the optical measurement system 200 of the second embodiment is equipped with optical measurement units 1 and a plurality of control devices 102. The optical measurement unit 1 includes "n" units. The plurality of control devices 102 are each connected to one or a plurality of optical measurement units 1 in a wireless communicable manner, and is allotted to optical measurement units 1 to control. Each optical measurement unit 1 is controlled by any one of the control devices 102. The device configuration itself of the optical measurement unit 1 and the control device 102 are the same as those of the first embodiment.

The plurality of control devices 102 are connected by a wired or wireless network 103 so that they can intercommunicate with each other. In the optical measurement system 200, it is configured such that among the plurality of control devices 102, any one of the control devices functions as a parent device (master device) 102a and control devices other than the parent device 102a function as child devices (slave devices) 102b. With this, in the optical measurement system 200, it is configured such that the parent device 102a relays the respective child devices 102b to perform the operation control of the simultaneous measurement of the optical measurement units 1 comprised of "n" devices.

Further, in the case of obtaining the state information 30, the parent device 102a transmits an instruction to request the state information 30 of the allotted optical measurement unit 1 to each child device 102b. In accordance with this instruction, each child device 102b obtains the state information 30 of the optical measurement unit 1. The operations of respective control devices 102 and optical measurement units 1 at the time of obtaining the state information 30 are the same as those in the aforementioned first embodiment. The obtained state information is transmitted from each child device 102b to the parent device 102a, the state information 30 of all optical measurement units 1 are obtained by the parent device 102a. As a result, the state display screen 40, the unit selection screen 50, etc., are displayed on the display unit 25 of the parent device 102a operated by a user.

The group 104 comprised of each control device 102 and the optical measurement unit 1 allotted to the control device 102 is arranged within a range in which a wireless communication can be performed. On the other hand, each group 104 can be arranged in the same room, or can be arranged in separate rooms, facilities, etc., in which no wireless communication is available. Accordingly, in the optical measurement system 200, for example, it is possible to arrange the group 104 of the parent device 102a in a laboratory office of a user and collectively arrange the group 104 of the child device 102b in another laboratories, and also possible to arrange the group 104 of the child device 102b in a remote location, such as, e.g., the home of the subject P. In cases where the control devices 102 are arranged in remote locations, the control devices 102 exchange control signals and/or measurement data 17a via a network 103, such as, e.g., the Internet.

Other configurations of the second embodiment are the same as those of the aforementioned first embodiment.

In the second embodiment, in the same manner as in the aforementioned first embodiment, it is possible to collectively confirm whether or not the respective optical measurement units 1 are in a state in which a measurement can be performed from the state information 30 displayed on the display unit 25 of the control device 102 (parent device 102a). Therefore, it is possible to shorten the time required for the measurement preparation by facilitating the grasping of the state of each optical measurement unit 1.

Further, in the optical measurement system 200 according to the second embodiment, by providing a plurality of control devices 102 connected in a state in which an intercommunication can be performed, the optical measurement units 1 are not restricted to be arranged within a wireless communication range of a single control device 102, and a simultaneous measurement can be performed using optical measurement units 1 arranged in separate rooms or remote locations to which a wireless signal does not reach. With this, it becomes possible to cope with various needs on simultaneous measurements by users.

It should be noted that the embodiments disclosed here are illustrative and non-restrictive in all aspects. The scope of the present invention is shown by not the aforementioned description of embodiments but by claims, and includes the meaning equivalent to claims and all modifications within the range of claims.

For example, in the first and second embodiments, a portable optical measurement unit 1 configured to be carried by a subject is exemplified, but the present invention is not limited to it. As an optical measurement unit, there is a large transportable unit having a built-in control device in a housing and a number of connectable probes more than the number of probes of a portable unit and configured to be carried by a carriage. In the present invention, in place of the portable unit, a transportable unit may be provided to the optical measurement system, and a portable unit and a transportable unit may be used together. Further, in the case of providing a transportable unit to the optical measurement system, a control device to be mounted in a transportable unit may be functioned as a control device of an optical measurement system.

In the aforementioned first and second embodiments, an example in which a plurality of optical measurement units 1 and a control device 2 are wirelessly connected is shown, but the present invention is not limited to it. In the present invention, a plurality of optical measurement units 1 and the control device 2 may be connected by wire.

Further, in the first and second embodiments, an example in which the state information 30 includes the information 32 on the communication state, the information 33 on the remaining battery capacity, the information 34 of the remaining memory capacity, and the receiving light quantity information 35 is shown, but the present invention is not limited to it. In the present invention, the state information may include only the information on communication state and the information on the remaining battery capacity. Further, in addition to the information on communication state, the information on remaining battery capacity, only one of the information on remaining memory capacity and the receiving light quantity signal information may be included in the state information. Further, the state information may include other information other than the information of these four items.

Further, in the aforementioned first and second embodiments, an example in which the state information 30 and the measurement availability information 31 on whether or not a simultaneous measurement can be performed are displayed on the display unit 25 (state display screen 40) every unit is shown, but the present invention is not limited to it. In the present invention, without displaying the measurement availability information, only the state information may be displayed. Even in this case, a user can judge whether or not each optical measurement unit can perform a simultaneous measurement from the state information display.

Further, in the aforementioned first and second embodiments, an example in which the state information 30 and the measurement availability information 31 are displayed in a ○/× form, but the present invention is not limited to it. In the present invention, the state information 30 and the measurement availability information 31 may be displayed in a manner other than the ○/× form. For the information 33 on the remaining battery capacity and the information 34 on the remaining memory capacity, a numerical display may be employed. For example, the remaining battery capacity may be displayed by percentage, and the remaining memory capacity may be numerically displayed with bite unit (MB). Further, for the information 32 on communication state and the measurement availability information 31, a character display may be employed. For example, the communication state may be displayed by "Good" or "Poor". Further, the measurement availability information may be displayed by "Measurable" or "Unmeasurable".

Further, in the first embodiment, for the convenience of explanation, the explanation was made using a flow-driven type flowchart in which processing is performed sequentially along the control processing flow, but the present invention is not limited to it. In the present invention, it may be carried out by an event-driven type processing that executes the processing per event unit. In this case, it may be carried out by a complete event-driven type and also can be carried out by a combination of the event-driven type and the flow-driven type.

BRIEF DESCRIPTION OF THE REFERENCE NUMERALS

1 optical measurement unit
2, 102 control device
21 control unit
24 communication unit
25 display unit
26 operation input section
30 state information
31 measurement availability information
32 information on communication state
33 information on remaining battery capacity
34 information on remaining memory capacity
35 received light quantity signal information
37 simultaneous measurement possible time
100, 200 optical measurement system

The invention claimed is:

1. An optical measurement system comprising:
a plurality of brain function optical measurement units, each of the plurality of brain function optical measurement units includes a battery, a holder that is mountable on a head of a subject, a plurality of light transmitting probes disposed in the holder, and a plurality of light receiving probes disposed in the holder, and a central processing unit (CPU) that is configured to control the plurality of light transmitting probes and the plurality of light receiving probes, and is configured to perform a brain function measurement on the subject; and
at least one control device configured to control the plurality of brain function optical measurement units,
wherein the at least one control device includes:
  a communication unit configured to receive, from each of the plurality of brain function optical measurement units, state information which includes at least information on a communication state between the brain function optical measurement unit and the control device on whether or not the brain function optical measurement unit is in a state in which the brain function optical measurement unit can perform a simultaneous measurement, and
  a control unit configured to determine whether each of the plurality of brain function optical measurement units can perform the simultaneous measurement or not based on the state information received, transmit an instruction to two or more of the plurality of brain function optical measurement units capable of performing the simultaneous measurement to perform the simultaneous measurement, and control the plurality of brain function optical measurement units so that the simultaneous measurement is performed by the two or more of the plurality of brain function optical measurement units simultaneously and in parallel for a plurality of subjects,
wherein the two or more of the plurality of brain function optical measurement units are configured to perform the simultaneous measurement based on the instruction transmitted from the control unit, and
wherein the state information includes information on a remaining battery capacity of the plurality of brain function optical measurement units.

2. The optical measurement system as recited in claim 1, wherein the control unit of the control device is further configured to collectively display information on whether or not the simultaneous measurement can be performed on a display for each of the plurality of brain function optical measurement units.

3. The optical measurement system as recited in claim 2, wherein the control device further includes an operation input section configured to receive individual selection operations selecting the two or more of the plurality of brain function optical measurement units capable of performing the simultaneous measurement.

4. The optical measurement system as recited in claim 1, wherein the state information further includes at least one of information on remaining memory capacity of the brain function optical measurement unit and information on a received light quantity signal of the brain function optical measurement unit.

5. The optical measurement system as recited in claim 1, wherein a control unit of the control device is further configured to calculate a measurement possible time for each of the plurality of brain function optical measurement units based on at least a remaining battery capacity of the brain function optical measurement unit, calculate a simultaneous measurement possible time when a simultaneous measurement is performed by the plurality of brain function optical measurement units based on respective measurement possible times for each of the plurality of brain function optical measurement units, and display the simultaneous measurement possible time on a display.

6. The optical measurement system as recited in claim 5, wherein the control unit of the control device is further configured to obtain the state information for each of the plurality of brain function optical measurement units during a measurement operation after an initiation of the simultaneous measurement, calculate the measurement possible time, and display information showing the brain function optical measurement unit in which the measurement possible time has become smaller that a predetermined value.

7. An optical brain function measurement method, comprising:
   obtaining state information which includes at least information on a communication state between a plurality of brain function optical measurement units and a control device on whether or not each of the plurality of brain function optical measurement units is in a measurable state;
   determining whether each of the plurality of brain function optical measurement units can perform a simultaneous measurement or not based on the state information; and
   controlling the plurality of brain function optical measurement units so that the simultaneous measurement is performed by two or more of the plurality of brain function optical measurement units simultaneously and in parallel for a plurality of subjects,
   wherein each of the plurality of brain function optical measurement units includes a battery, a holder that is mountable on a head of a subject, a plurality of light transmitting probes disposed in the holder, and a plurality of light receiving probes disposed in the holder, and a central processing unit (CPU) that is configured to control the plurality of light transmitting probes and the plurality of light receiving probes, and performs the simultaneous measurement on the subject, and
   wherein the state information includes information on a remaining battery capacity of the plurality of brain function optical measurement units.

8. The optical measurement system as recited in claim 1, wherein the at least one control device further comprises:
   a display configured to collectively display the state information received for each of the plurality of brain function optical measurement units.

* * * * *